United States Patent
Ueffing et al.

(10) Patent No.: US 11,229,651 B2
(45) Date of Patent: Jan. 25, 2022

(54) PROPHYLAXIS AND TREATMENT OF A NEURODEGENERATIVE DISEASE NOT BASED ON A PROTEIN-FOLDING DISORDER

(71) Applicant: Eberhard Karls Universität Tübingen Medizinische Fakultät, Tübingen (DE)

(72) Inventors: Marius Ueffing, Munich (DE); Blanca Arango-Gonzalez, Reutlingen (DE); Ana Griciuc, Somerville, MA (US)

(73) Assignee: Eberhard Karls Universitaet Tuebingen Medizinische Fakultaet, Tuebingen (DE)

( * ) Notice: Subject to any disclaimer, the term of this patent is extended or adjusted under 35 U.S.C. 154(b) by 0 days.

(21) Appl. No.: 15/082,409

(22) Filed: Mar. 28, 2016

(65) Prior Publication Data

US 2016/0213671 A1 Jul. 28, 2016

Related U.S. Application Data

(63) Continuation of application No. PCT/EP2014/070459, filed on Sep. 25, 2014.

(30) Foreign Application Priority Data

Sep. 27, 2013 (DE) ...................... 10 2013 110 714.1

(51) Int. Cl.
| | |
|---|---|
| *A61K 31/517* | (2006.01) |
| *A61K 31/4166* | (2006.01) |
| *A61K 31/00* | (2006.01) |
| *A61K 9/00* | (2006.01) |
| *A61K 31/4178* | (2006.01) |

(52) U.S. Cl.
CPC .......... *A61K 31/517* (2013.01); *A61K 9/0048* (2013.01); *A61K 31/00* (2013.01); *A61K 31/4166* (2013.01); *A61K 31/4178* (2013.01)

(58) Field of Classification Search
CPC ................ A61K 9/0048; A61K 31/517; A61K 31/4178; A61P 27/02
See application file for complete search history.

(56) References Cited

U.S. PATENT DOCUMENTS

| | | | | |
|---|---|---|---|---|
| 8,865,708 B2* | 10/2014 | Deshaies | ............ | A61K 31/4184 435/18 |
| 2010/0286091 A1* | 11/2010 | Wiestner | ................. | A61P 35/00 514/64 |

FOREIGN PATENT DOCUMENTS

| | | | |
|---|---|---|---|
| EP | 2 623 494 A1 | 8/2013 | |
| WO | WO-2009/011910 A2 | 1/2009 | |
| WO | WO-2011069039 A1 * | 6/2011 | ............. A61P 37/00 |
| WO | WO-2013/068431 A1 | 5/2013 | |

OTHER PUBLICATIONS

Schmidt et al. Current Neuropharmacology, 2008, vol. 6, pp. 164-178 (Year: 2008).*
Caffe et al., "Mouse Retina Explants After Long-Term Culture in Serum Free Medium", Journal of Chemical Neuroanatomy, vol. 22, 2001, pp. 263-273.
Griciuc et al., "Inactivation of VCP/ter94 Suppresses Retinal Pathology Caused by Misfolded Rhodopsin in *Drosophila*", PloS Genetics, vol. 6, Issue 8, Aug. 2010, 17 pages.
Arango-Gonzalez et al., "In Vivo and in Vitro Development of S- and M-Cones in Rat Retina", Investigative Ophthalmology & Visual Science, vol. 51, No. 10, Oct. 2010, pp. 5320-5327.
Valle et al., "Critical Role of VCP/p97 in the Pathogenesis and Progression of Non-Small Cell Lung Carcinoma", PloS One, vol. 6, Issue 12, Dec. 2011, 12 pages.
Chou et al., "Structure-Activity Relationship Study Reveals ML240 and ML241 as Potent and Selective Inhibitors of p97 ATPase", ChemMedChem, vol. 8, 2013, pp. 297-312.
Anonymous, "B6.CXB1-Pde6brd10/J", The Jackson Laboratory, Gefunden im Internet: URL:http://jaxmice.jax.org/strain/004297. html, Nov. 10, 2014, 6 pages.
Muraoka, "A Novel Valosin-Containing Protein Inhibitor Suppresses Photoreceptor Degeeration in a Rabbit Model of Retinitis Pigmentosa", Invest Ophthalmol Vis Sci, vol. 54, 2013, 2, pages.
Examination Report in EP Application No. 10 2013 110 714.1 dated Jun. 13, 2014, 6 pages.
Search Report and Written Opinion in International Application No. PCT/EP2014/070459 dated Dec. 2, 2014, 12 pages.
International Preliminary Report on Patentability in International Application No. PCT/EP2014/070459 dated Mar. 29, 2016, 16 pages.
Campello et al., "The Ubiquitin-Proteasome System in Retinal Health and Disease", Mol Neurobiol 47, 2013, pp. 790-810.
Search Report in EP Application No. 14777049.9 dated May 7, 2018, 5 pages.

* cited by examiner

Primary Examiner — James D. Anderson
(74) *Attorney, Agent, or Firm* — Marshall, Gerstein & Borun LLP

(57) ABSTRACT

The present invention relates to substances for the prophylaxis and treatment of a neurodegenerative disease which is not based on a protein-folding disorder. It further relates to substances for the stabilization of photoreceptors.

4 Claims, 2 Drawing Sheets

PROPHYLAXIS AND TREATMENT OF A NEURODEGENERATIVE DISEASE NOT BASED ON A PROTEIN-FOLDING DISORDER

CROSS-REFERENCES TO RELATED APPLICATIONS

This application is a continuation of co-pending International Patent Application PCT/EP2014/070459 filed on Sep. 25, 2014 and designating the United States of America, which was not published under PCT Article 21(2) in English, and claims priority of Germany Patent Application DE 10 2013 110 714.1 filed on Sep. 27, 2013, which are both incorporated herein by reference.

FIELD

The present invention relates to substances for the prophylaxis and treatment of a neurodegenerative disease which is not based on a protein-folding disorder. It further relates to substances for the stabilization of photoreceptors.

BACKGROUND

Neurodegenerative diseases form a group of mostly slowly progressing, hereditary or sporadically occurring diseases of the nervous system. The main feature is an increasing loss of nerve cells, resulting in various neurological symptoms which very often include dementia and movement disorders. The diseases can arise in different periods of life, which proceed diffusely or generalized and produce specific patterns of damage.

Of particular importance are neurodegenerative diseases of the eye.

The retinal degeneration is a decay of the retina which can finally result in the death of the cells of the retina. One of the most important forms of the retina degeneration is the so-called retinitis pigmentosa (RP) or also referred to as retinopathia pigmentosa. Worldwide about 3 million people are affected by RP, in Germany about 30,000 to 40,000. The disease mostly starts in the young age or the middle age with the first symptoms such as night blindness. The visual acuity gradually deteriorates. The whole process of the increasing visual impairment evolves insidiously and extends over decades in the person concerned.

The term "macular degeneration" refers to a group of neurodegenerative diseases of the eye which concern the macula lutea of the retina, also named the "yellow spot", accompanied with a gradual loss of function of the tissues present. The most important form is the age-related macular degeneration (AMD) in its dry and wet forms. It starts with depositions of so-called drusen, metabolic end products such as lipofuscins as well as an impaired blood circulation of the choroid, which can result in a so-called geographic atrophy. It can develop from the dry into the wet form where it may come to angiogenesis, oedema and bleeding into the retina. At an advanced stage both forms may transform into a flat cell death of the retinal pigment epithelium.

The diabetic retinopathy (DR) is a disease of the retina of the eye caused by the diabetes (diabetes mellitus). The increasing damage of small blood vessels causes an initially unnoticed damage of the retina. Here in the further course it may also come to oedema and bleeding all the way to a detachment of the retina. The DR may in the course of the disease result in blindness.

RELATED PRIOR ART

The available pharmacological therapeutic approaches against neurodegenerative diseases, in particular of such of the eye, are so far not satisfactory.

For example, the substances "ranibizumab" or "lucentis" as well as "VEGF trap" intended for the treatment of degenerative diseases of the eye in practice do have a limited spectrum of activity. In particular for hereditary retinal diseases as well as the dry form of the AMD such substances have no or a non-satisfactory effect.

In the prior art the group of the so-called VCP inhibitors are described for the treatment of neurodegenerative diseases. VCP stands for "valosin-containing protein". VCP, also referred to as p97, is a protein which is described as being involved in eukary-otic cells into the protein quality control and the removal of misfolded proteins.

In the WO 2013/068431 it is described the treatment of muscular atrophy due to mutated and misfolded SOD1 by means of the VCP inhibitors Eer-I, DBEQ, and Syk inhibitor III.

Griciuc et al. (2010), Inactivation of VCP/ter94 suppresses retinal pa-thology caused by misfolded rhodopsin in *Drosophila*, PLoS Genet. 6(8): e1001075, describe the suppression of retinal degeneration caused by misfolded rhodopsin by an inhibition of VCP.

Valle et al. (2011), Critical role of VCP/p97 in the pathogenesis and progression of non-small cell lung carcinoma, PLoS ONE 6(12): e209073, describe the inhibition of lung tumor cell proliferation and migration and induction of apoptosis by an inhibition of VCP.

Muraoka et al. (2013), A novel Valosin-containing protein inhibitor sup-presses photoreceptor degeneration in a rapid model of Retinitis pigmentosa, Poster Session ARVO annual conference Seattle 2013, describe the suppression of the photore-ceptor degeneration caused by misfolded rhodopsin by the application of VCP inhibitors.

In the EP 2 623 494 different VCP inhibitors are suggested for the treat-ment of glaucoma and retinitis pigmentosa which are based on protein-folding disorders.

Satisfactory pharmacological interventions for the treatment of such neurodegenerative diseases which are not based on a protein-folding disorder are so far not available in the state of the art.

SUMMARY OF THE INVENTION

Against this background it is an object of the present invention to provide a substance which is effective in the prophylaxis and/or treatment of a neurodegenerative disease which is not based on a protein-folding disorder. Another object of the present invention is to provide a substance for the stabilization of photoreceptors.

Such objects are met by the provision or use of an inhibitor of the valosin-containing protein (VCP inhibitor).

This finding was surprising and not to be expected. In the prior art it is described that VCP inhibitors can be used in neurodegenerative diseases which are based on a protein-folding disorder, for example on misfolded rhodopsin. It is not described that VCP inhibitors can also be effectively used in such neurodegenerative diseases which are not based on a protein-folding disorder.

The finding of the inventors was also not to be expected because VCP is described as such a protein which is directly involved into the protein folding machinery of the cell. According to the literature VCP is an ATP-driven chaperon which controls critical steps in the ubiquitin-depending protein quality control, extracts misfolded proteins from the endoplasmatic reticulum and directs them to the proteasomal degeneration. In the literature it is further already described that VCP colocalizes with misfolded rhodopsin.

It has therefore so far been assumed that VCP inhibitors do not show any effect in such neurodegenerative diseases which are not based on a protein-folding disorder.

According to the invention a "neurodegenerative disease which is not based on a protein-folding disorder" refers to such a neurodegeneration which is not caused by a mutation which would then result in a protein-folding disorder. Examples for this are the age-related macular degeneration (AMD) which occurs in progressing age and/or because of inflammatory events. Another example is the diabetic retinopathy (DR) which is based on an impaired cellular homeostasis and oxygen supply. This also includes the uveitis which is an inflammatory degenerative disease of the eye which can affect both the front and the rear section of the eye, including the retina. The invention also includes such neurodegenerative diseases which are based on a mutation or are caused by such, this mutation however does not result in a misfolding of the mutated protein but, if applicable, in other disorders or malfunctions of the affected protein.

According to the invention a "stabilization of photoreceptors" refers to counteracting the degeneration of a photoreceptor, either by preventing the degeneration or reducing the speed of degeneration.

The inventors could surprisingly realize by means of a representative number of different VCP inhibitors which were chemically and structurally different, that photoreceptors which were gained from wild-type rats remained functional in cell culture after the treatment with VCP inhibitors for a significantly longer period of time than non-treated photoreceptors. The degeneration of photoreceptors which can usually be found in cell cultures is significantly slowed down by the treatment with VCP inhibitors. The photoreceptors are surprisingly stabilized by the VCP inhibitors.

According to an embodiment of the invention the neurodegenerative disease is a disease of the eye, further preferably such a disease of the eye which is not based on a protein-folding disorder of a visual pigment, preferably of rhodopsin and/or opsin.

This measure has the advantage that a new therapeutic concept for an important group of neurodegenerative diseases is provided. The overwhelming majority of retinitis pigmentosa (RP) is not based on a protein-folding disorder of the rhodopsin or another visual pigment or protein, but can be ascribed to other causes. In such variants of RP the invention can provide remedy in an effective manner.

According to a further embodiment of the invention the disease of the eye is based on a degeneration of the pigment epithelium and/or retina degeneration, further preferred on a degeneration of the photoreceptor.

This measure has the advantage that for the very first time a therapeutically promising approach is provided which causes remedy for this important group of diseases of the eye which includes retinitis pigmentosa (RP).

In another embodiment of the invention the disease of the eye is selected from the group of retinitis pigmentosa (RP), age-related macular degeneration (AMD), in particular in its dry form, diabetic retinopathy (DR), primary or secondary retinopathy.

For the afore-mentioned diseases of the eye which are not based on a protein-folding disorder so far in the prior art no or only less satisfactory therapeutic options are available. For the first time the inventors herewith provide a new and promising therapeutic concept.

According to a further embodiment of the invention it is preferred if the VCP inhibitor is administered intraoculary, perioculary or systemically.

This measure has the advantage that depending on the kind of neurodegenerative disease in each case the optimum form of administration is selected.

In the use of the VCP inhibitor for the stabilization of photoreceptors according to the invention the proteins localized in the photoreceptor are, in an embodiment of the invention, present in the wild type, wherein the proteins localized in the photoreceptor are in a further embodiment visual pigments or rhodopsin and/or opsin.

This measure has the advantage that now for the first time with the VCP inhibitor also such photoreceptors can be stabilized which are not damaged by a mutation in a protein of the photoreceptor, such as an optical pigment, for example rhodopsin or opsin, or which are subject to a degeneration as a result. The stabilization rather occurs also in such cases where the degeneration is caused by other factors such as the increasing age, impaired cellular homeostasis or impaired oxygen supply as well as inflammation etc.

According to another embodiment of the use of the VCP inhibitor for the stabilization of photoreceptors according to the invention at least one of the proteins which is localized in the photoreceptor, such as an optical pigment, for example rhodopsin or opsin, comprises at least one mutation or genetic risk variant which does not result in a protein-folding disorder.

This measure has the advantage that now also the large group of the phenomena prevailing in the pathologies of the eye are captured, where a degeneration of the pigment epithelium of the photoreceptor can be observed, however the involved or causing mutations or genetic risk variants such as polymorphisms do not result in a protein-folding disorder but, if applicable, in a functional disorder of the affected protein.

According to a further embodiment of the use of the VCP inhibitor for the stabilization of photoreceptors according to the invention the proteins localized in the photoreceptor comprise visual pigments, further preferably rhodopsin and opsin.

This measure has the advantage that the invention can also be used for the stabilization of such photoreceptors where the most important photoreceptor proteins are present in the wild type or comprise such a mutation which results in a photoreceptor degeneration, however not in a folding disorder of rhodopsin.

Another subject-matter of the present invention is an inhibitor of the valosin-containing protein (VCP inhibitor) for the prophylaxis and/or treatment of a neurodegenerative disease which is not based on a protein-folding disorder.

The features, advantages, characteristics and further developments of the uses according to the invention likewise apply to the VCP inhibitor according to the invention.

Against this background another subject-matter of the present invention is a pharmaceutical composition for the prophylaxis and/or treatment of a neurodegenerative disease which is not based on a protein-folding disorder, comprising a VCP inhibitor as the active agent. Here the VCP inhibitor can be the only active agent. However additional active agents can be provided which may induce synergistic effects.

The pharmaceutical composition according to the invention is preferably configured for an intraocular, periocular or systemic administration. Typically, it can be in form of eye drops or but also as an injection solution or another pharmaceutical composition which may additionally contain pharmaceutically acceptable carriers as well as salts, buffers and further substances.

The features, advantages, characteristics and further developments of the uses according to the invention likewise apply to the pharmaceutical composition according to the invention.

Another subject-matter of the present invention is a method for the production of a pharmaceutical composition for the prophylaxis and/or treatment of a neurodegenerative disease which is not based on a protein-folding disorder, which comprises the formulation of a VCP inhibitor into a pharmaceutically acceptable carrier.

Pharmaceutically acceptable carriers are comprehensively described in the prior art and depend on the intended application form. An overview can for example be found in A. Kibbe, "Handbook of Pharmaceutical Excipients", 3rd Edition, 2000, American Pharmaceutical Association and Pharmaceutical Press. The content of this publication is a component of this application.

Another subject-matter of the present invention is a method for the prophylaxis and/or treatment of a neurodegenerative disease which is not based on a protein-folding disorder, comprising the administration of a VCP inhibitor or the pharmaceutical composition according to the invention, respectively, into a living being, preferably into or onto the eye of the living being.

The features, characteristics, advantages, and further developments of the uses according to the invention apply likewise to the methods according to the invention.

It is to be understood that the before-mentioned features and those to be explained in the following can be used not only in the indicated respective combination but also in other combinations or in isolated manner without departing from the frame of the present invention.

The invention will now be explained by means of embodiments which result in further characteristics, features, and advantages of the invention. The embodiments are purely illustrative and do not restrict the scope of the present invention. Reference is made to the enclosed figures which show the following:

DESCRIPTION OF PREFERRED EMBODIMENTS

Material and Methods

Ethics

Figure 1:
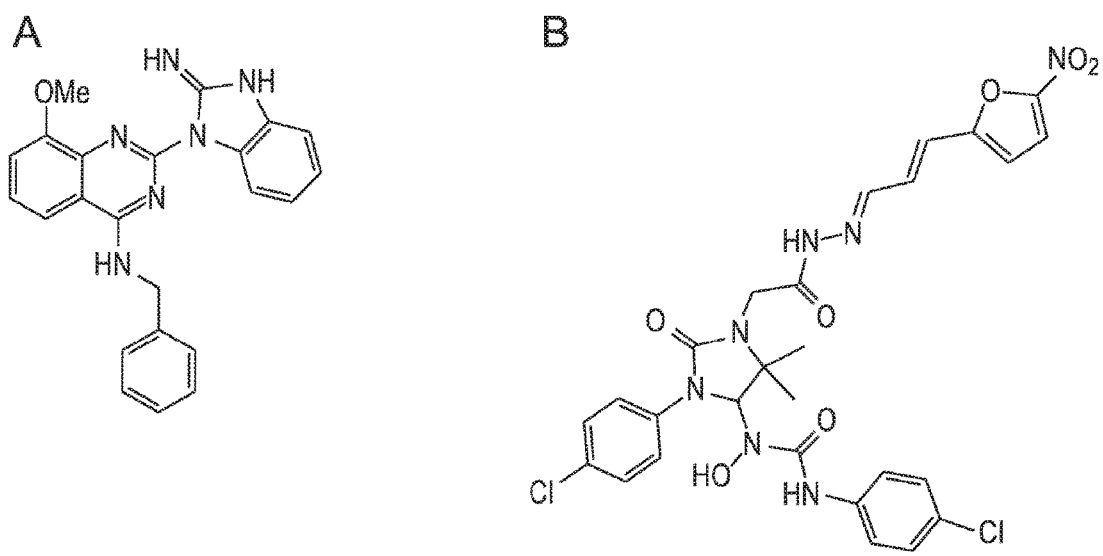
FIG. 1 shows the chemical structures of the VCP inhibitors ML240 (A) and Eeyarestatin I (EerI) (B).

All procedures were approved by the Tübingen University Committee on Animal Protection and performed in compliance with the Statement of the Association for Research in Vision and Ophthalmology ("AFO Statement"). The protocols are in compli-ance with § 4 paragraph 3 of the German Law on Animal Protection and were reviewed and approved by the "Einrichtung für Tierschutz, tierärztlicher Dienst and Labortierkunde". All efforts were made to minimize the number of animals used and their suffering.

Animals

Homozygous P23H rhodopsin transgenic rats (produced by Chrysalis DNX Transgenic Sciences, Princeton, N.J., United States of America) of the line Tg (P23H) 1 Lay (P23H-1) were kindly provided by Dr. M. M. LaVail (University of California, San Francisco, Calif., United States of America) and bred in the Animal Housing Facility in the Center for Ophthalmology in Tübingen. Heterozygous P23H rats were employed, obtained by crossing with wt, CD rats (CDH IGS rat; Charles River, Germany) to reflect the genetic background of autosomal-dominant retinitis pigmentosa (ADRP).

Experimental Animals

Retinas of postnatal day 9 (PN9) of P23H transgenic rats were cultivated for six days (DIVE) that correspond to PN15, i.e. the peak of degeneration in in vivo aged-matched mutants. The day of birth was denoted as P0. For radial sections, cultures were immersed in 4% paraformaldehyde in 0.1 M phosphate buffer (PB; pH 7.4) for 30 minutes at 4° C. and embedded in cryomatrix (Tissue-Tek, Leica, Bensheim, Germany). The radial sections (15 µm thick) were processed immediately or stored at 20° C.

Preparation of Organ Cultures

The retinas were isolated from nine-days-old P23H rats with the retinal pigment epithelium (RPE) attached essentially as described previously in Caffe et al. (2001), "Mouse retina explants after long-term culture in serum free medium", J. Chem. Neuroanat. 22(4): 263-73, and Arango-Gonzalez et al. (2010), "In vivo and in vitro devel-opment of S- and M-cones in rat retina", Invest. Ophthalmol. Vis. Sci. 2010 October; 51(10):5320-7. Briefly, the eyes of decapitated rats were enucleated in aseptic environment and pretreated with 12% proteinase K (ICN Biomedicals Inc., OH, United States of America) for 15 minutes at 37° C. in R16 serum-free culture medium (Invitrogen Life Technologies, Paisley, United Kingdom). The enzymatic digestion was stopped by the addition of 20% fetal bovine serum. Retina and RPE were dissected and four radial sections were made to flatten the tissue. The tissue was transferred to a 0.5 µm polycar-bonate membrane (Corning Life Sciences, Lowell, Mass., United States of America), with the RPE facing the membrane. The inserts were placed into six well culture plates and incubated with R16 nutrient medium at 36.5° C. The retina was left in R16 culture medium without a treatment for one day to allow an adaptation to the culture conditions. The medium was changed at DIV1, DIV3, and DIV5, and the new medium either contained ML240 (1 µM or 200) or EerII (1 µM or 20 µM). Both components were pre-diluted in dimethyl sulfoxide (DMSO, Sigma). For controls, the same amount of DMSO (0.05% or 1% respectively) was diluted in culture medium. The cultures were fixed at DIVE and analyzed as radial sections.

TUNEL Assay

A TUNEL assay ("terminal deoxynucleotidyl transferase dUTP nick end labeling") was performed using in situ cell death detection kit conjugated with fluorescein isothiocyanate (Roche Diagnostics, Mannheim, Germany).

Immunohistochemistry

The sections were incubated over night at 4° C. with primary antibodies against rhodopsin or visual arrestin. The fluorescence immunocytochemistry was per-formed using Alexa Fluor® 488 and 564 conjugated secondary antibodies (Molecular Probes, Inc., Eugene, United States of America). Negative controls were carried out by omitting the primary antibody.

Results

Figure 2:
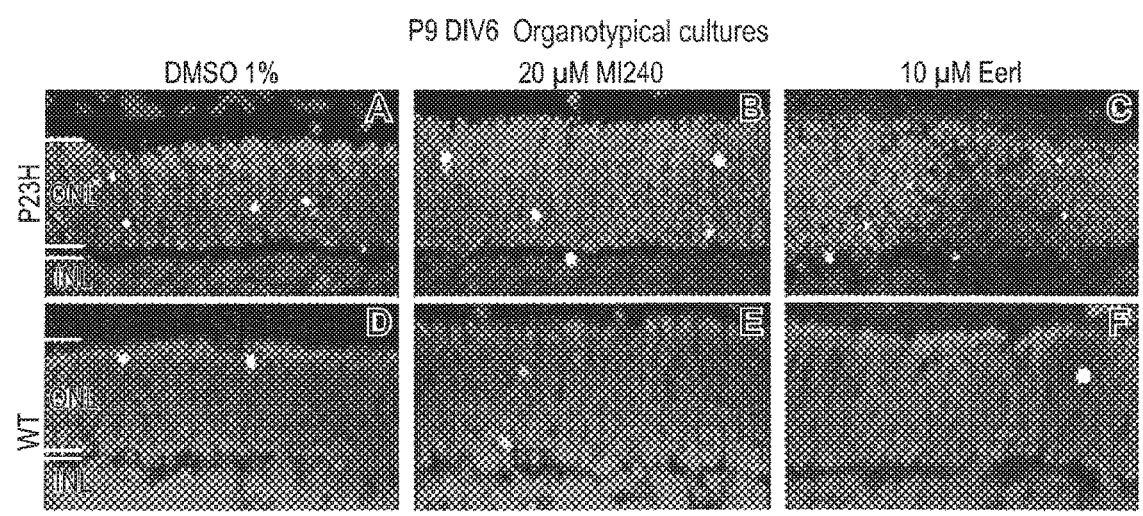
FIG. 2 shows fluorescent microscopic images of a TUNEL assay for dying cells. Retinal organ cultures which were obtained from rats being mutated in the rhodopsin (P23H) and wild-type rats were treated with ML240 (B and E) and EerI (C and F). The controls were treated with DMSO. Radial sections were prepared from the cultures and a TUNEL staining was made.

Retinal organ cultures were obtained from rats mutated in rhodopsin (P23H) and wild-type rats. The P23H mutation in the rhodopsin of the rat corresponds to the P37H mutation in humans ($Rh1^{P37H}$) resulting in misfolded rhodamin and a form of RP. These organ cultures were treated with the VCP inhibitors ML240 (FIG. 1A) and EerI (FIG. 1B). The radial sections prepared herefrom show a significant increase of the survival of such photoreceptors and a reduced TUNEL staining of such retinas which were treated with ML240 (FIGS. 2; B and E) and EerI (FIGS. 2; C and F), in comparison to the control which were only treated with DMSO (FIGS. 2; A and D).

Figure 3:
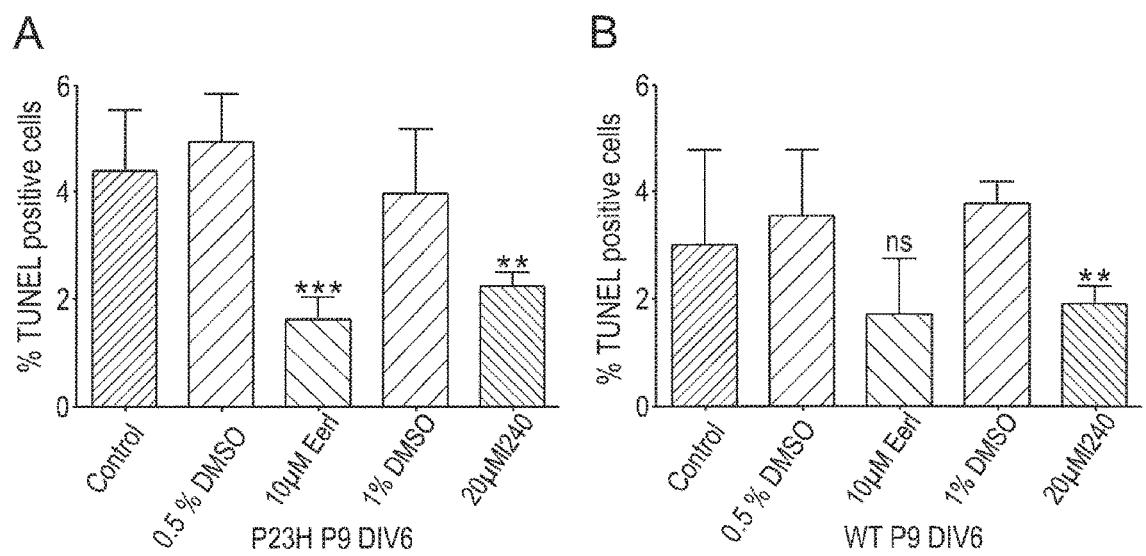
FIG. 3 shows a bar chart with the result from FIG. 2, i.e. the photoreceptor cell death in cultivated retinas which obtained from rats mutated in the rhodopsin (P23H) (A) and wild-type rats (B) in dependence of the VCP inhibitors ML240 and EerI. It is shown the percentage of TUNEL positive cells in the outer nuclear layer (ONL) in comparison to the total amount of nuclei in the ONL.

As expected, it can be seen that in the P23H mutant both VCP inhibitors, i.e. EerI but also ML240, significantly reduce the amount of dying photoreceptors in comparison to the correspondingly untreated and DMSO treated (0.5 and 1%) controls (FIG. 3; A). Surprisingly, the VCP inhibitors also reduce in WT cultivated retinas the percentage of TUNEL positive cells, ML240 significantly and EerI not significantly (FIG. 3; B); $p<0.01$; *$p<0.001$. The VCP inhibitors, therefore, have also a stabilizing effect to "healthy" photoreceptors which do not comprise a mutation in its proteins.

CONCLUSION

The inventors were able to demonstrate in an impressive manner by means of a retina explant system that VCP inhibitors exert a stabilization on photoreceptors, the proteins of which are present in the wild type or are not folding mutated. This results to the inventive conclusion that VCP inhibitors can be used for the prophylaxis and/or treatment of a neurodegenerative disease which is not based on a protein-folding disorder, and for the stabilization of photoreceptors.

Therefore, what is claimed, is:

1. A method of treating a neurodegenerative disease of the eye selected from the group consisting of age-related macular degeneration (AMD), AMD in its dry form, and diabetic retinopathy (DR), the method comprising administering an inhibitor of valosin-containing protein (VCP inhibitor) or a pharmaceutical composition comprising a VCP inhibitor as an active agent to a living being afflicted by said neurodegenerative disease of the eye.

2. The method of claim 1, wherein the VCP inhibitor is present in a formulation selected from the group consisting of eye-drop solution, intraocularly administrable preparation, systemically administrable preparation, and nutritional supplement.

3. The method of claim 1, comprising administering the VCP inhibitor or the pharmaceutical composition into the eye of the living being.

4. The method of claim 1, wherein the VCP inhibitor is selected from the group consisting of ML240 and Eeyarestatin I.

* * * * *